(12) United States Patent
Lawshe et al.

(10) Patent No.: US 12,414,562 B2
(45) Date of Patent: Sep. 16, 2025

(54) MOISTURIZING LIQUID COMPOSITION WITH CATIONIC BIOCIDE

(71) Applicant: Henkel AG & Co. KGaA, Duesseldorf (DE)

(72) Inventors: Jessica Lawshe, Phoenix, AZ (US); Janice L. Fuls, Fountain Hills, AZ (US); Gregory Cole, Stamford, CT (US)

(73) Assignee: Henkel AG & Co. KGaA, Duesseldorf (DE)

( * ) Notice: Subject to any disclaimer, the term of this patent is extended or adjusted under 35 U.S.C. 154(b) by 963 days.

(21) Appl. No.: 17/068,053

(22) Filed: Oct. 12, 2020

(65) Prior Publication Data

US 2021/0022337 A1 Jan. 28, 2021

Related U.S. Application Data

(63) Continuation of application No. 15/829,363, filed on Dec. 1, 2017, now abandoned.

(51) Int. Cl.
| | | |
|---|---|---|
| *A01N 33/12* | (2006.01) | |
| *A01N 39/00* | (2006.01) | |
| *A61K 8/27* | (2006.01) | |
| *A61K 8/34* | (2006.01) | |
| *A61K 8/362* | (2006.01) | |
| *A61K 8/40* | (2006.01) | |
| *A61K 8/41* | (2006.01) | |
| *A61K 8/42* | (2006.01) | |
| *A61Q 17/00* | (2006.01) | |
| *A61Q 19/00* | (2006.01) | |
| *A61Q 19/10* | (2006.01) | |

(52) U.S. Cl.
CPC .............. *A01N 33/12* (2013.01); *A01N 39/00* (2013.01); *A61K 8/27* (2013.01); *A61K 8/345* (2013.01); *A61K 8/362* (2013.01); *A61K 8/40* (2013.01); *A61K 8/416* (2013.01); *A61K 8/42* (2013.01); *A61Q 17/005* (2013.01); *A61Q 19/10* (2013.01); *A61Q 19/007* (2013.01)

(58) Field of Classification Search
CPC .......... A01N 33/12; A01N 39/00; A61K 8/27; A61K 8/345; A61K 8/362; A61K 8/40; A61K 8/416; A61K 8/42; A61Q 17/005; A61Q 19/10; A61Q 19/007
See application file for complete search history.

(56) References Cited

U.S. PATENT DOCUMENTS

2015/0148425 A1 * 5/2015 Fuls ..................... A01N 25/30
2017/0275569 A1 * 9/2017 Pegelow ............... C11D 3/386

FOREIGN PATENT DOCUMENTS

WO    WO 2016/091688 A1 * 6/2016 ............. C11D 3/386

OTHER PUBLICATIONS

Philip L. Gould, Salt selection for basic drugs, International Journal of Pharmaceutics, 1986, 33:201-217. (Year: 1986).*
Johnson W, Heldreth and B, Bergfeld WF, et al. Final Report of the Cosmetic Ingredient Review Expert Panel on the Safety Assessment of Pelargonic Acid (Nonanoic Acid) and Nonanoate Esters. International Journal of Toxicology. 2011;30(6_suppl):228S-269S. (Year: 2011).*
James R. Schwartz. Journal of Drugs in Dermatology. 2016; 15(2):140-144. (Year: 2016).*
Marks R, Pearse AD, Walker AP. The effects of a shampoo containing zinc pyrithione on the control of dandruff. Br J Dermatol. Apr. 1985; 112(4):415-22. (Year: 1985).*
Jang HJ, Shin CY, Kim KB. Safety Evaluation of Polyethylene Glycol (PEG) Compounds for Cosmetic Use. Toxicol Res., 2015, 31(2):105-136 (Year: 2015).*
Krishna R Raghupathi et al. Size-Dependent Bacterial Growth Inhibition and Mechanism of Antibacterial Activity of Zinc Oxide Nanoparticles. Langmuir, 2011, 27, 7, 4020-4028 (Year: 2011).*

* cited by examiner

*Primary Examiner* — Joseph K McKane
*Assistant Examiner* — David M Shim
(74) *Attorney, Agent, or Firm* — Blank Rome LLP

(57) ABSTRACT

A liquid cleaning composition including: at least 80 wt. % liquid solvent; a cationic quaternary amine biocide; and a non-cationic, amine oxide moisturizing agent.

16 Claims, 1 Drawing Sheet

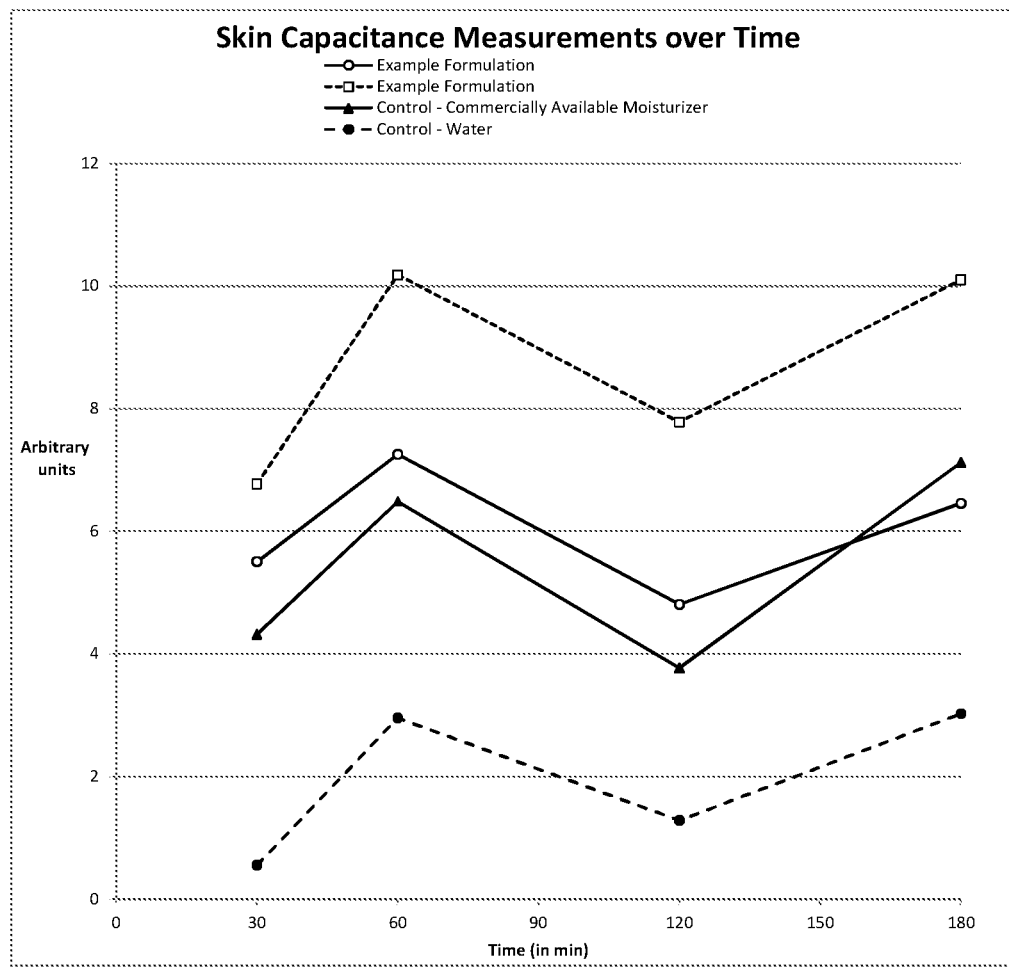

MOISTURIZING LIQUID COMPOSITION WITH CATIONIC BIOCIDE

BACKGROUND OF THE INVENTION

Soaps and synthetic detergents may be used as cleaning compositions. Liquid soap formulations are popular with consumers for such applications as washing human skin. Surfactants in the formulations, including soaps and synthetic detergents, increase the ability of aqueous solutions to carry hydrophobic materials such as oils, fats, and greases. Surfactants are chemicals with both a hydrophilic domain and a hydrophobic domain. Surfactants orient themselves on the boundary between hydrophobic material and the water environment. This reduces the free energy of the hydrophobic material and increases the carrying capacity of hydrophobic material in the aqueous solution.

BRIEF DESCRIPTION OF THE DRAWINGS

FIG. 1 shows the results of a lower leg controlled application test (LCAT) for two example and two control compositions as assessed with a corneometer.

DETAILED DESCRIPTION OF THE INVENTION

Cleaning formulations are assessed using a variety of parameters. These may include: cleaning, dry feeling, tight feeling, oil removal, conditioning, anti-bacterial effectiveness, anti-viral effectiveness, material cost, production cost, stability, fragrance or lack thereof, etc. As in any development activity, balancing the different design parameters to produce a desirable product is a challenge, in part because optimization of one parameter may result in lack of optimization of different parameters.

There is ongoing demand for products with strong anti-bacterial and/or anti-virial properties, which may also be referred to as biocidal activity. These products see use in homes, offices, and many businesses, including medical facilities. The use of cleaning formulations to reduce bacteria and virus fragments, especially on hands, is an important part of medical practice. However, the compositions of many anti-bacterial and anti-viral products make them hard on skin, resulting in dryness, chapping, and cracking, which discourage use and/or produce other health hazards.

Accordingly, it is desirable to have a liquid cleaning composition which combines anti-bacterial and anti-viral properties with skin conditioning. The challenge is that skin conditioning components have a tendency to inactivate or reduce the effectiveness of the anti-bacterial and/or anti-viral component(s). Further, there are not effective predictive models for when combinations will retain their functionality. Instead, much of the work in this area is experimental in nature.

Investigation into forming a liquid composition which retains functionality of a quaternary amine biocide and/or a cationic biocide has been challenging. Soaps include anionic surfactants, such as synthetic and natural soaps. Quaternary amines are cationic species due to the quaternary amine with its positive charge. Under a variety of conditions, free energy of the system is minimized by coupling the positive and negative charges producing a complex with low solubility and little biocidal activity. The presence of anionic surfactants and quaternary amines in a solution allows rearrangement to minimize the free energy of the system, which can reduce the availability and effectiveness of cationic biocides over time as they couple with anionic species in the formulation.

Similarly, when looking to add conditioning agents, the inventors initially theorized that conditioners with quaternary formulations similar to the quaternary amines would allow the quaternary amines to retain their biocidal activity. This proved to be incorrect, although the reason and mechanism for why the presence of cationic conditioners inhibits the functionality of the quaternary amines is not clear. However, further investigation uncovered other conditioning agents that were compatible with both the anionic surfactants (synthetic surfactants and carboxylic acid soaps) and the quaternary amines (biocides). These discoveries allowed formulation of a liquid cleaning composition with both biocidal and conditioning properties.

All numbers used in this specification and the associated claims should be treated as having the implied precision unless a precision is otherwise noted. The implied precision of a number is half the value of the least significant digit. Thus, the implied precision of 10 is +/−5 units and would be understood to cover a range of 15 to 5 units, while the implied precision of 11 is +/−0.5 units and would be understood to include a range from 10.5 to 11.5 unless otherwise noted. Recited ranges and values should be understood to cover the entire range of the implied precision unless otherwise recited. If needed, scientific notation using the symbol "E" for exponent of a power of ten will be used to assure the desired specificity. So, "5E1" indicates 50, while "5.0E1" indicates 50 where the zero is a significant digit.

As used in this specification and the associated claims, the term "unmodified" when applied to a molecule or class of molecules indicates that those molecules have not been functionalized with another functional group outside the group or groups defining the base molecule. Thus, an "unmodified" polyglycol contains only the basic ether links and the organic segments and does not have a fatty chain added, an amine, etc.

As used in this specification and the associated claims, the term "substantially free" indicates that none of that material is added to the composition for the purpose of formulating and/or modifying the composition. Accordingly, substantially free does not require the composition be completely free of the named component. For example, incidental formation in situ and/or incidental contamination in feed materials do not make a composition not "substantially free." The term substantially free in intended to distinguish formulations which may, unavoidably and/or for economic reasons, include detectable amounts of, for example, alcohols. The ability to detect very low concentrations of species using mass spectroscopy, FTIR, AES, and similar mechanisms requires the ability to reasonably distinguish formulations with a significant amount of a material from detectable trace amounts of the material.

Among other examples, this specification describes a liquid cleaning composition, the composition including: at least 80 wt. % liquid solvent; a cationic quaternary amine biocide; and a non-cationic moisturizing agent, wherein the composition reduces bacteria by at least 2.0 log 10 when assessed using ASTM E1174 and reduces drying of the stratum corneum compared with a water control between 30 and 180 minutes after application.

Among other examples, this specification also describes a liquid cleaning composition, the composition including: at least 80 wt. % water; a first cationic quaternary amine biocide; a second cationic quaternary amine biocide; and an unmodified polyglycol, wherein the composition reduces bacteria by at least 2.0 log 10 when assessed using ASTM E1174 and reduces drying of the stratum corneum compared with a water control between 30 and 180 minutes after application as assessed with a lower leg controlled application test (LCAT).

This specification also describes a liquid cleaning composition, the composition including: at least 80 wt. % water; 0.06 wt. % to 1 wt. % of a cationic biocide; 0.7 wt. % to 3 wt. % glycerin; 0.01 wt. % to 5 wt. % of a polycarboxylic acid and/or salt thereof; and 0.01 wt. % to 1 wt. % myristamidopropylamine oxide.

In an example, a moisturizing, biocidal, liquid cleaning formulation has the following composition (all percentages are wt. % of the formulation):

Example 1

| | |
|---|---|
| Benzalkonium Chloride and/or Benzethoium Chloride | 0.11 to 0.26 wt. % |
| Hydroxypropyl Methylcellulose | 0.25 wt. % |
| Tetrasodium EDTA | 0.02 wt. % |
| Lauramine Oxide | 1.49 wt. % |
| Lauramidopropylamine Oxide | 1.64 wt. % |
| Glycerin | 1.50 wt. % |
| Citric Acid | 0.70 wt. % |
| Sunflowerseedamidopropyl Ethyldimonium Ethosulfate and PEG-9 | 0.80 wt. % |
| Preservative | 0.22 wt. % |
| Cetrimonium Chloride | 0.7-2.77 wt. % |
| Cocamidopropyl Betaine | 0.400 wt. % |
| Trideceth-9 | 0.28 wt. % |
| Myristamidopropylamine Oxide | 0.19 wt. % |
| PEG-9 | 0.21 wt. % |
| PEG-5 Isononanoate | 0.19 wt. % |
| Zinc Sulfate | 0.05-0.1 wt. % |
| Fragrance | 0.02-0.25 wt. % |
| Dyes | 0.00001-0.000038 wt. % |
| Aqua (Water, Eau) | Q. S. |

Example 1 shows a variety of specific components. However, substitution of similar species can be used to produce similar products. Example 1 includes a cationic biocide. In some examples, these are quaternary amine biocides, for example: benzalkonium chloride (BAC), benzethonium chloride (BZC), cetrimonium chloride (CC), and/or cetrimonium bromide (CTAB) may be used individually and/or in combination. More complex structures, such as bisbiguanides, e.g., chlorhexidine and polymeric biguanides, e.g., polyhexamethylene biguanide may be used as cationic biocides either by themselves and/or in conjunction with one or more quaternary amine biocides. Example 1 includes both cetrimonium chloride with benzalkonium chloride and/or benzethonium chloride. In some examples, the use of multiple cationic biocides at a lower total concentration may be more effective than the use of a single species at a higher total concentration.

Example 1 also includes non-ionic surfactants. These have a hydrophobic domain and a hydrophilic domain. The hydrophilic domain lacks formal charges being assigned to any of the associated groups in the hydrophilic domain. The hydrophobic domain may be provided by a "fatty" region, often a hydrocarbon, for example, an alkyl chain. The hydrophillic region may be provided by a poly-oxide. Polyglycols are a common hydrophilic domain due to their ability to incrementally adjust the properties of the non-ionic surfactant by adjusting the length of the polyglycol. In some examples, the number of repeat units (generally, ethylene glycol or propylene glycol units) in a polyglycol is indicated by a number. For example, PEG-5 Isononanate indicates five polyethylene glycol (PEG) groups attached to an isononanate residue.

Polyethylene glycols such as PEG-9 may provide a number of different desirable properties to a formulation. They may decrease the evaporation rate; they may stabilize the formulation and prevent separation. They may be used to modify the viscosity of the formulation. Polyglycols are often used because the ability to tune their properties by adjusting the chain length independent of the wt. percentage provides an additional variable to tune properties of a formulation.

Polysaccharides may be used to fill similar roles in a formulation. For example, celluloses, guar, starches, xanthan gum, and components with a number of oxygen containing groups may perform similar roles in increasing water retention, reducing surface energy, and/or modifying viscosity. Generally, these replacements are higher molecular weight molecules such as polyglycols and/or polysaccharides. The substitution with smaller polyols, e.g., glycol, propane diol, etc. produces a larger impact due to the smaller size of the smaller polyols.

In some examples, a saccharide, cellulose, or similar large polyol may be modified by adding a fatty chain to increase its usefulness as a non-ionic surfactant. Hydrocarbon (or alkyl) modified cellulose and hydrocarbon modified (or alkyl) modified saccharides are commercially available. Such species include at least one sugar moiety and at least one hydrocarbon moiety. The hydrocarbon may be an alkyl chain. The hydrocarbon may be an unsaturated hydrocarbon. The sugar may be a polycyclic sugar. The sugar may include multiple sugar moieties of the same base sugar. The sugar may include multiple types of sugars.

Some amide and amine-oxide fatty substances are compatible with maintaining activity of a cationic biocide and obtaining acceptable moisturization. These substances include a hydrophilic domain and a fatty domain which allows them to function as surfactants. $C_8$ to $C_{24}$ amides and amine-oxides are useful in forming formulations with both biocidal and moisturizing properties. Preferred species include: $C_8$ to $C_{14}$ amine oxides and amidoalkyl oxides. More complex amine containing components may also be used to provide moisturizing without compromising the effectiveness of the cationic biocide. For example, cocamidopropyl betaine, or its constituents such as lauramidopropyl betaine, is a larger molecule with multiple nitrogens and oxygens. The ratio of polar groups (e.g., —OH, —NH) to non-polar groups (e.g., $CH_2$) or total weight provides a way to assess different amine/amide structures against each other. This is similar to assessing HLB using Griffin's method but does not provide the kind of individualized assessment of bond polarity in Davies' method. However, this approach does provide a straightforward metric to use to compare different structures of fatty amides, fatty amine-oxides, etc. The cleaning composition may include a mixture of different fatty amides and fatty amine-oxides. The use of multiple components allows form more degrees of freedom in optimization of the desired properties of the cleaning formulation. Fatty amides and amine-oxides may be 0.2 to 12 wt. % of the cleaning composition. In an example, fatty amides and amine-oxides constitute 2 to 6 wt. % of the cleaning composition.

Other nonionic surfactants may be useful to providing moisturizing without compromising the effectiveness of the cationic biocide. For example, fatty alcohols, especially $C_8$ to $C_{22}$ alcohols may be useful in this regard. fatty alcohols may be unsubstituted or substituted. Fatty alcohols may be saturated, unsaturated, or polyunsaturated. Fatty alcohols may be linear or branched. Some preferred fatty alcohols include: cetyl alcohol, stearyl alcohol, and myristyl alcohol. If present, fatty alcohols may constitute from 0.001 to 5 wt. % of the formulation.

Fatty acids may also be included in the cleaning composition. The fatty alcohols may be unmodified. The fatty alcohols may include a polyglycol domain. Fatty acids have a hydrophilic domain in the carboxyl group and a fatty chain. Fatty acids, as used herein, refers to $C_6$ to $C_{22}$ monocarboxylic acids. Fatty acids may have a terminal carboxyl group. In other cases, the carboxyl group is located somewhere else on the fatty chain, for example, toward the center of the fatty chain. The fatty chain may be saturated, unsaturated, and/or polyunsaturated. The fatty chain may be linear or branched. In some examples, mixing multiple fatty alcohols with different numbers of unsaturated bonds in their respective fatty chains produces improved solubility over the use of a single fatty alcohol. For example, a mixture of linoleic acid and linolenic acid, both $C_{18}$ fatty acids, is useful in improving the moisturizing property of a cleaning composition. If present, fatty acids may constitute from 0.001 to 8 wt. % of the formulation.

The formulation may include one or more polycarboxylic acids. Polycarboxylic organic acids as used herein refers to organic molecules of fourteen or fewer carbons with at least two carbonyl groups ($-CO_2H$) and/or salts thereof ($-CO_2X^+$). Polycarboxylic acids and/or their salts may serve a variety of roles in cleaning compositions. Polycarboxylic acids may function as chelators and increase the solubility of ions or soils. Polycarboxyllic acids have localized electronegativity which increases their solubility in water but may also have organic domains, allowing them to reduce surface energy and modify the activity of surface active species. The carboxyl groups may buffer the formulation, helping to reduce changes in pH, for example when contacting skin. While any suitable polycarboxylic acid may be used in the liquid cleaning formulations, preferred species include: citric acid, ethylenediaminetetraacetic acid (EDTA), oxalic acid, and/or maleic acid and salts thereof. The availability of polycarboxylic acids with increasing numbers of carbon atoms allows adjustment of the properties. For example, the dicarboxlic acid series: oxalic acid, succinic acid, glutaric acid, adipic acid, pimelic acid, suberic acid, azelaic acid, sebacic acid, etc. allows tailoring of both the pKas of the carboxylic acids as well as the hydrophilic-lipophilic balance (HLB). While the pKa of the acids converges with the larger dicarboxylic acids, adding an electron-donating or electron-withdrawing group near one or more of the carboxyl groups allows further tuning of the Pka values of the acid groups. Similar flexibility is available with other polycarboxylic acid families. Further, the ability to mix and match polycarboxylic acids provides additional degrees of freedom for tuning formulation properties. Polycarboxylic acids may constitute up to 7 wt. % of a cleaning composition. In an example, polycarboxylic acids are 0.02% to 1.4 wt. % of a cleaning composition.

Zinc compounds provide zinc ions in the formulation. Zinc ions have biocidal properties. Zinc is provided as zinc sulfate in Example 1. However, other sources of zinc ions may be substituted with predictable effects. For example, zinc may be provided as a complexed species such as zinc picolinate, zinc citrate, zinc acetate, zinc glycerate, zinc gluconate, and/or zinc monomethionine. Zinc may be provided in other forms for example, ZnCl, ZnI, ZnO, etc. In one example, the zinc is provided both as an ionic species and as a nanoparticle. Suitable nanoparticles may have a longest mean axis length of 30 nm, with averages from 20 to 60 nm enhancing antibacterial activity. Zinc compounds may be present from 0.00001 to 1.8 wt. % of the formulation. In one example, an ionic zinc compound constitutes 0.02 to 0.8 wt. % of the formulation.

Example 1 is a water based formulation. Example 1 is substantially free of low molecular weight monoalcohols (for purposes of this specification, monoalcohols with five or fewer carbons). The lack of low molecular weight monoalcohols may improve the moisturization of the skin. The use of hand sanitizers with high alcohol content may be associated with chapping and drying of the hands. Water may constitute at least 60 wt. %, 70 wt. %, 80 wt. % and/or 90 wt. % of the formulation. In an example, a cleaning composition is no less than 92 wt. % water.

This specification also covers formulations which include low molecular weight ($C_1$ to $C_8$) monoalcohols. The use of monoalcohols may increase the biocidal activity of the formulation. The formulation may include a mixture of one or more low molecular weight monoalcohols and water as the solvent. Replacing a portion of the water with a monoalcohol may increase the drying rate of the formulation (or reduce the drying time). In one example, ethanol is used as the low molecular weight alcohol. Other low molecular weight monoalcohols may be used. A mixture of multiple low molecular weight monoalcohols may be used with or without water as the solvent in the formulation. In an example, the inclusion of a low molecular weight alcohol facilitates mixing and homogeneity of the formulation. The inclusion of $C_1$ to $C_5$ monoalcohols may reduce the moisturization produced by a formulation. In some examples, up to 20 wt. % of the formulation may be low molecular weight monoalcohols substituted for water.

The Health Care Personnel Hand Wash (ASTM E1174) is a standardized method that measures the reduction of *Serratia marcescens* following a hand washing episode using prototype compositions. Briefly, the hands are inoculated with $1.0 \times 10^9$ cfu/hand of *Serratia marcscens*. Bacterial concentrations may be expressed in colony forming units (cfu). Hands are then placed in sterile bags and 75 mL of stripping solution is added. The hands are massaged for 1 minute. A sample is taken and plated using standard plate methods to determine the number of bacteria on the hands. This is considered the baseline. The hands are then inoculated again followed by a hand washing treatment. Hands are washed for thirty seconds and then rinsed for thirty seconds. The bacteria recovery step is repeated. The difference in the bacteria found after treatment compared to baseline is calculated and reported as the log 10 reduction. Generally speaking, reductions of less than 1 order of magnitude (1.0 log 10) are considered low and/or inactive. Reductions of 1 to 2 orders of magnitude are considered indicative of biocidal activity but below acceptable levels to characterize as effective. Results of greater than 2 orders of magnitude reduction (2.0 log 10) are considered evidence of effectiveness. The FDA in the 1994 tentative final monograph expects a minimum 2.0 log reduction following a single wash.

When assessed using ASTM E1174, formulation 1A) a base with 0.13 wt. % benzalkonium chloride (BAC) had a 2.18 log 10 reduction. A non-antibacterial hand soap control 1B) produced a 1.80 log 10 reduction. A physiological saline rinse 1C) produced a 1.89 log 10 reduction.

An effort to formulate a composition that was less hard on hands was hindered by the tendency of many moisturizing components to reduce the effectiveness of the biocide. For example, formulation 1D) base with increased glycerin (by 1.4%), linoleic acid, linolenic acid, tocopherol & hydroxethyl Urea produced a 1.53 log 10 reduction. Similarly, formulation 1E) base with increased glycerin (by 1.4%), linoleic acid, linolenic acid, and tocopherol had a 1.63 log 10 reduction. The reduced efficacy, as measured by ASTM E1174, shows the challenges of maintaining biocidal activity when moisturizing components are added.

Efforts to use cationic moisturizing components were similarly unsuccessful. Formulation 1F) base with increased glycerin (by 1.4%) and Polyquaternium-7 produced 1.66 log 10 reduction. Formulation 1G) Base with increased glycerin (by 1.4%), Polyquatnum-10, and Guar Hydroxypropyltrimonium Chloride similarly showed lower effectiveness (1.81 log 10) compared with the 1A formulation without moisturizing components. Accordingly, the many moisturizing components, including Polyquaternium cationic polymers reduced biocidal activity compared with controls.

A formulation 1H) which included Base with increased glycerin (by 1.4%) and myristamidopropyl PG-dimonium chloride phosphate had a result of 1.89 log 10. While not any better than the baseline saline control, this formulation at least was not worse than the baseline control. Formulation 1H also suggested some amine and/or amide conditioning agents may not hinder the effectiveness of quaternary amine biocides.

Continued efforts identified formulation 1I) Base with increased glycerin (by 1.4%) and increased lauramidopropylamine oxide from 1.5% to 1.8%, and Symolliant® W/S, produced acceptable results with a 2.17 log 10 reduction Replicate testing of this formulation produced 2.10 log 10 reduction again as measured using ASTM E1174.

Symolliant® W/S is a mixture of water, pentylene glycol, glycerin, fructose, urea, citric acid, sodium hydroxide, maltose, sodium pyrrolidone carbonic acid (Na PCA), sodium chloride, sodium lactate, trehalose, allentoin, sodium hyaluronate, and glucose.

The formulations were evaluated using a Lower Leg Controlled Application Test (LCAT). LCAT is a technique that can reliably discriminate the moisturization potential of personal cleansing or leave-on products used under normal use conditions. Materials that occlude the skin or enhance lipids can increase skin hydration and/or improve skin barrier function. Test objective is to assess and compare the relative moisturization potential of personal cleansing products by visual and instrumental evaluations. Moisturization is demonstrated by showing benefit effects when compared to water. This procedure also allows for testing of multiple products on a given subject, increasing the statistical power of the comparison.

For the described LCAT testing, six test sites (5 cm×5 cm) are marked on the outer aspect of lower legs of each subject. Each test site is washed with the assigned test product or is washed with water as a control. Visual evaluations for dryness are taken at baseline to qualify. Instrument (E.g., Skicon and/or Corneometer) readings are taken for relative skin hydration at baseline, 30 minutes, 1 hour, 2 hours and 3 hours after a single wash. To generate the following results, approximately 20 women participated in the study. Subject ages were between 18-55 years of age.

A corneometer uses a dielectric measurement of the skin to calculate a water level (hydration) of the skin. Successive measurements allow monitoring of the amount of water in the skin over time. A moisturizing product is one that enhances retention of water in the skin over time. In contrast, when products without the moisturizing quality are used, the skin dries over time. The use of a water-only rinse provides a negative control representing no moisturizing. In some data sets, a known product with adequate moisturizing provides a positive control. Positive and negative controls provide baselines to validate test results for the current environmental conditions and test subject conditions.

Example 1 and compositions 1H and 1I produced significantly ($p<0.05$) higher water retention in stratum corneum compared with a water control. Several of the other compositions produced significant moisturizing, however, as discussed above, they did not provide at least 2.0 log reduction as assessed by ASTM E1174.

Turning now to the FIGURES, FIG. 1 shows an example of a LCAT for two exemplary formulations and two controls. The first control was a commercially available moisturizing bar without significant antibacterial properties. The second control was a water rinse control. Statistical significance vs. the water control was demonstrated at all time points (30 min through 180 min) with p value of less than 0.05. In many of the data points, the p value of the test vs. the water control was below 0.01 and below 0.001. Accordingly, the skin treated with the liquid cleaning composition showed reduced moisture loss in the stratum corneum compared with both the water control and the commercial product control between 30 and 180 minutes after treatment. The same products also demonstrated at least 2.0 log 10 reduction when tested using ASTM E1174. Accordingly, this demonstrates that the biocidal activity of a cationic biocide can be combined with selected moisturizing agents to produce a product capable of both moisturizing and killing bacteria as a liquid cleaning composition.

It will be appreciated that, within the principles described by this specification, a vast number of variations exist. It should also be appreciated that the examples described are only examples, and are not intended to limit the scope, applicability, or construction of the claims in any way.

The invention claimed is:
1. A liquid cleaning composition comprising:
   at least 80 wt. % water;
   0.06 wt. % to 1 wt. % benzalkonium chloride;
   0.7 wt. % to 3 wt. % glycerin;
   0.01 wt. % to 5 wt. % of a polycarboxylic acid and/or a salt thereof;
   0.01 wt. % to 1 wt. % myristamidopropylamine oxide;
   0.5 wt. % to 5 wt. % cetrimonium chloride;
   PEG-5 isononanoate;
   1.5 wt. % to 1.8 wt. % lauramidopropylamine oxide; and
   0.02 wt. % to 0.8 wt. % of zinc sulfate nanoparticles having an average axis length of between 20 nm and 60 nm,
   wherein the composition reduces bacteria by at least 2.0 log 10 when assessed using ASTM E1174.
2. The composition of claim 1, wherein the polycarboxylic acid and/or the salt thereof comprises three carboxyl groups per molecule.
3. The composition of claim 1, wherein the polycarboxylic acid and/or the salt thereof comprises an acid selected from the group consisting of citric acid, a citrate salt, ethylenediaminetetraacetic acid (EDTA), an EDTA salt, oxalic acid, an oxalate salt, and any mixture thereof.
4. The composition of claim 1, wherein the composition comprises at least 90 wt. % water.
5. The composition of claim 1, further comprising an unmodified polyethylene glycol of 5 to 18 $C_2H_4$ repeating units linked by ether bonds.
6. The composition of claim 1, further comprising 0.001 wt. % to 5 wt. % of fatty amides.

7. The composition of claim 6, wherein the fatty amides are selected from the group consisting of cocamidopropyl betaine, lauramidopropyl betaine, and a mixture thereof.

8. The composition of claim 1, further comprising a non-ionic surfactant.

9. The composition of claim 1, wherein the composition reduces drying of the stratum corneum with a water control between 30 and 180 minutes after application as assessed with a lower leg-controlled application test.

10. The composition of claim 1, wherein the composition is substantially free of mono-alcohols with five or fewer carbons.

11. The composition of claim 4, wherein the composition comprises at least 92 wt. % water.

12. A liquid cleaning composition comprising:
at least 92 wt. % water;
0.11 wt. % to 0.26 wt. % benzalkonium chloride;
about 1.5 wt. % glycerin;
about 0.7 wt. % citric acid;
about 0.19 wt. % myristamidopropylamine oxide;
about 1.64 wt. % lauramidopropylamine oxide;
0.7 wt. % to 2.77 wt. % cetrimonium chloride;
about 0.19 wt. % PEG-5 isononanoate; and
0.05 wt. % to 0.1 wt. % zinc sulfate nanoparticles having an average axis length of between 20 nm and 60 nm.

13. The composition of claim 12, wherein the composition reduces bacteria by at least 2.0 log 10 when assessed using ASTM E1174.

14. The composition of claim 12, wherein the composition further comprises:
about 0.4 wt. % cocamidopropyl betaine; and
about 0.21 wt. % PEG 9.

15. The composition of claim 1, wherein the zinc sulfate nanoparticles have a longest mean axis length of 30 nm.

16. The composition of claim 12, wherein the zinc sulfate nanoparticles have a longest mean axis length of 30 nm.

* * * * *